Figure 1:
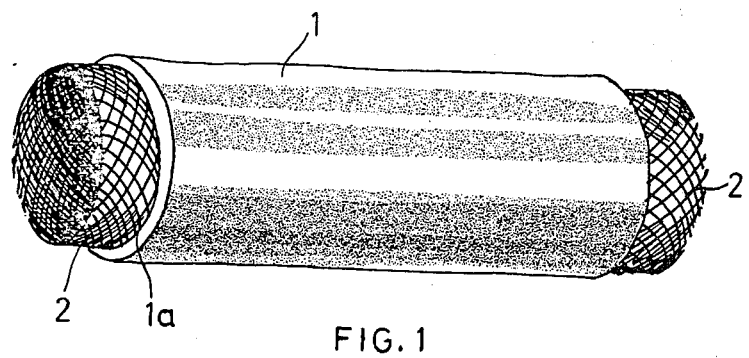

United States Patent [19]

Eriksson et al.

[11] 4,416,028

[45] Nov. 22, 1983

[54] BLOOD VESSEL PROSTHESIS

[76] Inventors: Ingvar Eriksson, Ycklinge, Rasbokil; Staffan Bowald, Fiskartorpet, Rasbo, both of S-755 90 Uppsala; Christer Busch, Nya Valsätravägen 17B, S-752 46 Uppsala, all of Sweden

[21] Appl. No.: 230,942

[22] PCT Filed: Jun. 4, 1980

[86] PCT No.: PCT/SE80/00161
§ 371 Date: Jan. 22, 1981
§ 102(e) Date: Jan. 22, 1981

[87] PCT Pub. No.: WO80/02641
PCT Pub. Date: Dec. 11, 1980

[51] Int. Cl.³ ............................................... A61F 1/24
[52] U.S. Cl. ....................................................... 3/1.4
[58] Field of Search ................... 3/1.4, 1; 128/334 R, 128/335.5, 334 C

[56] References Cited

U.S. PATENT DOCUMENTS

| | | |
|---|---|---|
| 3,105,492 | 10/1963 | Jeckel ........................................ 3/1.4 |
| 3,425,418 | 2/1969 | Chvapil et al. ....................... 3/1.4 X |
| 3,463,158 | 8/1969 | Schmitt et al. ........................ 3/1 X |
| 4,130,904 | 12/1978 | Whalen .................................... 3/1.4 |

FOREIGN PATENT DOCUMENTS

| | | | |
|---|---|---|---|
| 1491218 | 4/1969 | Fed. Rep. of Germany .......... 3/1.4 |
| 1018288 | 1/1966 | United Kingdom .................... 3/1.4 |

*Primary Examiner*—Ronald L. Frinks
*Attorney, Agent, or Firm*—Bacon & Thomas

[57] ABSTRACT

A blood vessel prosthesis, comprising a tubular element of an inert, completely or partially non-resorbable material having no adverse tissue reaction. To the inside of the tubular element an interior wall construction of a resorbable material with no adverse tissue reaction is fixed, which wall construction has such a structure that passage of blood cells, such as erythrocytes and thrombocytes, into or through the same is permitted.

10 Claims, 7 Drawing Figures

BLOOD VESSEL PROSTHESIS

This application is based upon International Application No. PCT/SE80/00161, filed June 4, 1980.

The present invention relates to a new type of blood vessel prosthesis for permanent or long-term implantation, which has clearly improved properties compared to previously used substitutes.

A variety of substitutes for pathologically changed, functionally important arteries and veins have been utilized in surgical treatment. Thus, either autologous material (such as superficial veins from the lower extremities), non-autologous biological material (such as chemically or physically treated blood vessels from other persons or from animals) or synthetic materials (such Dacron and Teflon ® tubes having varying structures depending on method of preparation) have been commonly used. As substitutes for aorta and large branch arteries the synthetic materials have proved to give acceptable results. As substitutes for extremity arteries or arteries of a corresponding dimension the body's own veins have proved to give by far the best results. In many cases, however, the patient has no suitable vein material, and attempts have therefore been made to use a non-autologous material or a completely synthetic material. Such arterial reconstructions have, however, given inferior results. The factor above all contributing to the less favourable result is the absence of development of the specific inner coating characterizing a blood vessel, the intimal layer. The normal intimal layer consists of a cell layer, whose functions are on one hand to prevent the formation of intravascular thrombi (anti-thrombogenic effect), and on the other hand to provide for exchange of metabolic products between the blood and smooth muscle cells in the vascular wall. On the inner aspect of the hitherto used vascular substitutes no endothelium is developed, but it is coated by a layer of fibrin and sometimes connective tissue. The resulting surface certainly appears to be smooth but lacks potent anti-thrombogenic properties. There is therefore a risk for formation of a thrombus, which may obstruct the inserted prosthesis completely with serious ischemic consequences for the patient. Essentially the same conditions will apply when replacing pathologically changed veins.

Previous attempts to attain an inner endothelial coating on synthetic vascular prostheses have been unsuccessful. This problem has now been solved through the present invention.

It has been found that such an endothelial coating can be obtained by implantation of a vascular prosthesis composed of a completely or partially non-resorbable synthetic material, the inside of which is essentially covered by an inner wall construction of a resorbable material. To obtain the endothelium layer, the resorbable inner wall material should have such a porous structure that blood cells, such as erythrocytes and thrombocytes, may pass into or through it, so that it can serve as or define a growth zone or zones for the new tissue. Hereby a relatively thick and uniform layer of thrombotic material can be formed, building a scaffold for the proliferation of a endothelium coated muscle layer. Preferably the resorbable material is arrranged so that more or less continuous interspaces are formed within the resorbable material and/or between the resorbable and the at least partially non-resorbable materials. This can, for example, be achieved by spacing, preferably large, parts of the resorbable material from the non-resorbable material.

The resorbable layer or covering can be designed and applied in different ways. Thus, the resorbable material may, for example, be an inner tubular member, which is inserted into and fixed to the outer tubular prosthesis element of non-resorbable material. The inner tube may be formed of a coarse-to fine-meshed net, or may be a tube with perforated walls or walls having pores, etc. The resorbable structure may e.g. further consist of a fine wire structure protruding from or fixed to the outer tubular member or be another correspondingly porous structure of a resorbable material, e.g a spongy layer. The attachment of the resorbable covering to the non-resorbable member may, of course, also take place before the prosthesis material is formed into a tube. It is also possible to cover the non-resorbable surface with the resorbable material by a method providing the necessary interspaces or growth zones as well as the necessary blood-cell pervious structure of the resorbable material. More detailed examples of the arrangement of the resorbable structure will be described below.

To increase the thickness of the fibrin layer which in the initial stage after the implantation is to be retained by the resorbable material, two or possibly more, at least partially, mutually separated layers of resorbable material may be applied or, alternatively, a relatively thick layer with sufficient porosity or perforation may be used. The resorbable net, tube etc. can be fixed to the non-resorbable prosthesis sleeve in different ways, e.g. with resorbable sutures or glue.

At least the inside of the outer non-resorbable member ought to be micro-porous, porous or provided with holes in order to promote the attachment of the re-formed tissues. Tubular prosthesis members of everything from a coarse-meshed net to a tube with fine pores may be used. A suitable and well-functioning vascular prosthesis according to the invention can e.g. consist of a per se conventional vascular prosthesis, on whose inside one or more nets of a resorbable material have been applied.

The above mentioned interspaces between non-resorbable and resorbable material in the vascular prosthesis can each have a greater or lesser extent, but the total area of these interspaces should preferably be so large that it approaches the size of the inner surface of the outer non-resorbable material layer, i.e. those portions or points where the resorbable material for fixing to the non-resorbable material contacts the latter should be as small as possible. The distance between the material surfaces in these interspaces or growth zones should be at least about $10\mu$ to permit penetration of the blood cells, but is should suitably not exceed about 5 to 10 mm even for large prostheses. Preferably said distance is about 0.5 to 3 mm, depending, of course, also on the size of the blood vessel to be replaced.

The resorbable material should be non-toxic without adverse tissue reaction, be resorbed at such a rate that a satisfactory reformation of tissue is permitted and not give rise to a fibrous scar tissue. A number of such materials are previously known and are described in the literature. As examples polyglycolic acid (PGA), co-polymers of glycolic acid and lactic acid, and various lactide polymers may be mentioned. Polyglycolic acid can essentially be considered as a product of polymerization of glycolic acid, that is hydroxyacetic acid, which in simplified form is shown by the equation:

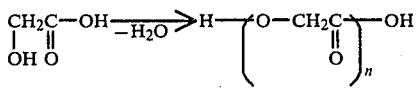

Preferably n is such that the molecular weight is in the range from about 10,000 to about 500,000. Such polyhydroxy acetic esters are described in e.g. U.S. Pat. No. 3,463,158, which is incorporated by reference herein. Copolymers of glycolic acid and lactic acid are described e.g. in U.S. Pat. No. 3,982,543, which is incorporated by reference herein, the copolymer containing 15–85 mole percent glycolic acid and the remainder lactic acid and possibly small amounts of additional momomers. Homopolymers and copolymers of lactic acid are described e.g. in U.S. Pat. No. 3,636,956, which is incorporated by reference herein. These polylactide compositions contain up to about 15 percent by weight of repeating units of the formula:

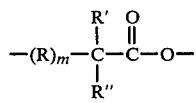

wherein R is lower alkylene, preferably methylene or ethylene, m is 0 or 1, R' is hydrogen or lower alkyl, R" is hydrogen or alkyl of up to about 22 carbon atoms when m is 0, and hydrogen or lower alkyl when m is 1, and can be the same as R' or different. Preferred are units derived from α-hydroxycarboxylic acids and particularly comonomer units derived from glycolide or DL-lactide. Examples of suitable comonomers are glycolide, β-propiolactone, tetramethylglycolide, β-butyrolactone, γ-butyrolactone, pivalolactone, and intermolecular cyclic esters of α-hydroxybutyric acid, α-hydroxiisobutyric acid, α-hydroxyvaleric acid, α-hydroxyisovaleric acid, α-hydroxycapronic acid, α-hydroxy-α-ethylbutyric acid, α-hydroxyisocapronic acid, α-hydroxy-β-methylvaleric acid, α-hydroxyheptanoic acid, α-hydroxyoctanoic acid, α-hydroxydecanoic acid, α-hydroxymyristic acid, α-hydroxystearic acid and α-hydroxylignoceric acid. In the particular case with glycolide as comonomer the polylactide composition may contain about 35 mole percent of repeating units derived therefrom.

The manufacture of various surgical products, such as suture wire, suture net, etc. based upon the above mentioned materials is also described in the literature. Examples of commercially available suture materials are e.g. Polyglactin 910 (VICRYL®, Ethicon, Sommerville, N.J., U.S.A.), which is a copolymer containing 90% glycolic acid and 10% lactic acid and DEXON® (Davis & Geck, Pearl River, N.Y., U.S.A.) which consists of polyglycolic acid. Of course, also other materials can be used provided that they have the desired properties according to the above.

As the material for the non-resorbable prosthesis part essentially any conventional body-acceptable, non-resorbable material usually used for similar purposes may be used. Examples of such materials are polyethylene terephthalates, such as Dacron and Terylene, (e.g. micro-porous expanded) polytetrafluoroethylene (TEFLON®), linear polyethene, isotactic polypropene, nylon, etc. This non-resorbable prosthesis part may as mentioned above be manufactured in various fabric forms (knitted, woven, possibly provided with outer and inner velour surfaces) or as a more or less porous tube. Optionally the non-resorbable material may be combined with a resorbable material, e.g. be made of wires or fibres of a non-resorbable material coated with a resorbable material, be woven with the interspersion of wires of resorbable material, have the inside coated by a resorbable material layer etc. Of course, also other materials having such properties that permit implantation may be used.

The prosthesis covering of resorbable material ought to be such that the absorption thereof in the organism takes at least 20 days, and preferably 40–150 days.

The blood vessel prosthesis according to the invention will now be described in more detail by means of the following description of some specific non-limiting embodiments, reference being made to the accompanying drawing, wherein FIG. 1 is a perspective view of an embodiment of a vascular prosthesis according to the invention, and FIGS. 2 to 7 are schematic fragmentary sectional views of alternative embodiments of the invention.

Figure 2:
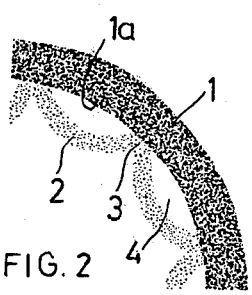

The vascular prosthesis shown in FIG. 1 comprises an outer tube 1 of a porous essentially non-resorbable material, and an inner covering or tube 2 of a resorbable material. The inner tube 2 is in the figure formed of a net, which is attached to the outer tube 1 by means of a number of (not shown) sutures of a resorbable material. The covering 2 contacts the outer tube 1 only at the fixing points, and the net portions therebetween remain spaced from the inner surface 1a of the tube 1—as is schematically shown in FIG. 2—and form the above mentioned growth zones, to which the blood cells after implantation can pass via the meshes of the net 2. The mesh size of the net 2 is not critical as such but mesh sizes up to about 5×5 mm can conveniently be used.

As mentioned above it is, for example, possible to replace the net 2 with a tubular element of a more or less (e.g. micro-porous) porous material. Of course, both the outer tube 1 and the covering 2 may consist of nets, it also being possible to use woven or knitted materials. Further, the inner tube 2 can be a porous tube structure, while the outer tube 1 is a tubular net. The fixing of the inner tube or covering 2 and the outer tube 1 can also be performed in another way than is shown above, e.g. by gluing with a suitable material. The distance between the tube surface 1a and the covering 2 is suitably chosen such that it is about 0.5–3 mm.

The thickness of the muscle cell/endothelium layer which is to be formed can be varied, e.g. by using several nets 2 separated by a suitable interspace as above. In the case that the inner tube 2 is a porous tube, the thickness of the latter can be varied, it being understood, however, that the porosity according to the above should be sufficient for good penetration of the blood cells. The thicknesses of the outer tube 1 and the covering layer 2 are suitably chosen such that the outer tube 1 corresponds to the outer layer of connective tissue (adventitia) and the layer 2 corresponds to the muscle cell and endothelium layer of the blood vessel or blood vessel part to be replaced by the vascular prosthesis. In the same way as in the case of nets it is possible to use several mutually separated layers of a porous material.

FIGS. 2 to 7 schematically show some variations of the design and application of the inner wall construction 2 to the outer tube 1. Thus, in FIG. 2 the resorbable material structure 2 is supposed to be a net (as in FIG. 1) or another porous flexible structure which remains spaced to the outer tube 1 between fixing points 3, so that interspaces 4 are formed between the respective portions of the inner wall 2 and the outer tube 1. (The inner wall 2 may, of course, also be a more rigid resorbable structure designed and fixed in the above manner.) As mentioned above the fixing means may e.g. be resorbable sutures or glue.

Figure 3:
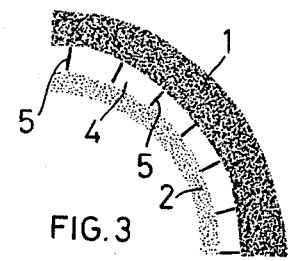
Figure 4:
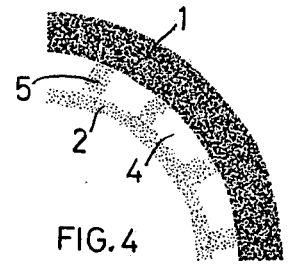

In FIG. 3 a tubular resorbable structure 2 having a smaller diameter than the inner diameter of the outer tube 1 is fixed to the latter through projections 5 of non-resorbable material extending from the outer tube 1, so that an interspace 4 is formed between the tubes. FIG. 4 shows a similar arrangement, but here the projections or connecting elements 5 protrude from the resorbable structure 2.

Figure 5:
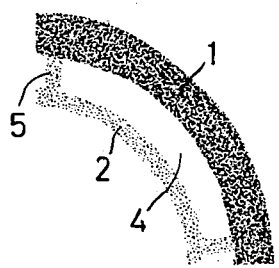

In FIG. 5 the connecting parts 5 are fewer and thus more spaced apart. The connecting elements or parts 5 may be arranged and designed in any suitable way. Thus, they may have a small wire-like dimension, and be uniformly or non-uniformly distributed along the material surfaces 1 and 2 in any suitable manner. They may, however, also have larger dimensions and can, for example, form partition walls or structures extending e.g. radially or circumferentially.

Figure 6:
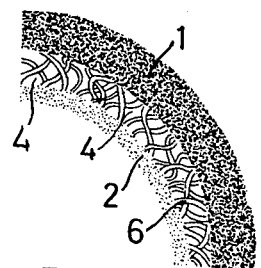
Figure 7:
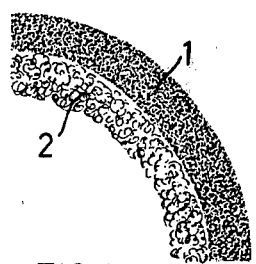

In FIG. 6 an inner tube or covering 2 is fixed to the outer tube 1 through a more porous or loose layer 6, e.g. a wire structure, of a resorbable or partially resorbable material. In FIG. 7, finally, the resorbable covering 2 is applied to the outer tube 1 without any proper spacing as above, and consists of a structure of a more porous nature, such as a fine wire-structure of loop or skein type, or of a highly porous or spongy material. The layer 2 may further be e.g. a wire-structure in the form of a "nail or pin carpet" or the like having pins or wire protruding from a layer of a resorbable material applied to the non-resorbable material.

The embodiments shown in FIGS. 1 to 7 are, as mentioned hereinbefore, only examples of various ways of providing the resorbable material, and further variations, such as various combinations of the above described examples are naturally possible within the invention.

In animal tests with the new vascular prosthesis according to the invention it has been found that an endothelium layer as well as an underlying cell layer of smooth muscle tissue is developed on the inside of the synthetic non-resorbable vascular prosthesis material. The reformed layer on the inside of the synthetic material is developed in a short time through regeneration of normal constituents of the vascular wall from the edges of the animal's own vessels, while at the same time the resorbable material disappears. The reformed endothelium presents properties characteristic of a normal endothelium. Thus, after the healing process is completed the grafted vessel segment consists of an outer part of synthetic material, which gives a sufficient strength to the vessel, and of an inner part of body tissue having the structure of a normal vessel. Thus, the vascular prosthesis according to the invention essentially functions as a normal blood vessel.

The invention is further illustrated by means of the subsequent examples of animal tests with a vascular prosthesis according to the invention (corresponding to the variant shown in FIGS. 1 and 2), but it is, of course, in no way whatsoever restricted to the special prosthesis design used herein.

EXAMPLE 1

A vascular prosthesis was produced by applying a net of Polyglactin 910 (Vicryl ®, Ethicon, Sommerville, N.J., U.S.A.) on the inside of tube of expanded polytetrafluoroethylene (Impra Inc., Phoenix, Ariz., U.S.A.) having a length of 10 cm and an inner diameter of 13 mm. The net had a wire size of $140\pm20\mu$ and a pore thickness of $400\times400\mu$ and was attached to the PTFE tube with polyglactin sutures. The tube thus constructed was then sewn into pig thorax aorta as a replacement for an excised section.

The implanted tube functioned quite satisfactorily, and six weeks after the operation the animal was slaughtered and the implanted portion taken care of for microscopic examination. The latter showed that the polyglactin net had been practically completely resorbed. At the place of the net a considerable layer of smooth muscle cells had grown in, and the inside of this layer was covered by endothelial cells.

EXAMPLE 2

A vascular prosthesis was produced as above, using as the outer tube a double velour knitted Dacron ® tube (Meadox Medicals, Oakland, N.J., U.S.A.) of the same length as above and with an inner diameter of 10 mm and as the inner tube a polyglactin net of the same type as in Example 1. The net was attached to the outer tube with polyglactin sutures. With this device the same experiment as in Example 1 was then performed. The result after six weeks' implantation totally corresponded to the result of Example 1.

EXAMPLE 3

A similar tube construction as in Example 1 was produced, a tube of Dacron fabric with a wire thickness of about $20\mu$ and a mesh size of about $600\times600\mu$ being used as the outer tube, and the inner tube consisting of a polyglactin net of the same type as in Example 1. With this device the same experiment on pig as in Example 1 was then performed. The result after six weeks' implantation totally corresponded to the results in Example 1.

The invention is, of course, not restricted to the above specially described and shown embodiment, but many modifications and variations are possible within the scope of the subsequent claims. This applies especially to the resorbable and non-resorbable materials, the design of covering and outer tube, the dimensioning of the various components etc.

We claim:

1. A blood vessel prosthesis comprising a tubular support member of an at least partially non-resorbable material without adverse tissue reaction, and at least one inner wall member of a resorbable material without adverse tissue reaction supported by said tubular member and forming a substantially concentric inner wall structure thereto, said inner wall structure being sufficiently porous to permit the passage of blood cells, such as erythrocytes and thrombocytes, through the free inner surface and into at least a substantial part of the thickness thereof, thereby providing a support inside said tubular support member for the formation of a layer of thrombotic material whereby an endothelium coated muscle layer is formed on said tubular support member.

2. A blood vessel prosthesis as claimed in claim 1, wherein said at least one inner wall member at least partially is spaced apart from said tubular member, thereby defining interspaces between the tubular member and said inner wall member, into which interspaces blood cells can pass.

3. A blood vessel prosthesis as claimed in claim 2, wherein the distances between the material surfaces in said interspaces amount to 10μ–5 mm.

4. A blood vessel prosthesis as claimed in claim 1, wherein said at least one inner wall member comprises at least one layer of a porous material.

5. A blood vessel prosthesis as claimed in claim 1, wherein said at least one inner wall member comprises at least one tube of net material.

6. A blood vessel prosthesis as claimed in claim 1, wherein the resorbable material is selected from the group consisting of polyglycolic acid, copolymers of glycolic acid and lactic acid, and lactide polymers and copolymers.

7. A blood vessel prosthesis as claimed in claim 1, wherein said tubular support member is porous.

8. A blood vessel prosthesis as claimed in claim 6, wherein said tubular member is woven or knitted.

9. A blood vessel prosthesis as claimed in claim 1, wherein the material of said tubular member is selected from the group consisting of polyethylene terephthalates, polytetrafluoroethane, polyethane and polypropene.

10. A method of replacing blood vessels or parts thereof, comprising the step of implanting a blood vessel prosthesis, comprising a tubular support member of an at least partially non-resorbable material without adverse tissue reaction, and at least one inner wall member of a resorbable material without adverse tissue reaction supported by said tubular member and forming a substantially concentric inner wall structure thereto, said inner wall structure being sufficiently porous to permit the passage of blood cells, such as erythrocytes and thrombocytes, through the free inner surface and into at least a substantial part of the thickness thereof, thereby providing a resorbable support inside said tubular support member for the formation of a layer of thrombotic material whereby an endothelium coated muscle layer is formed on said tubular support member.

* * * * *